United States Patent [19]

Ikushima et al.

[11] Patent Number: 5,403,739
[45] Date of Patent: Apr. 4, 1995

[54] METHOD FOR ESTERIFICATION OF (S)-CITRONELLOL USING LIPASE IN SUPERCRITICAL CARBON DIOXIDE

[75] Inventors: Yutaka Ikushima; Norio Saito; Kiyotaka Hatakeda; Shota Ito, all of Sendai, Japan

[73] Assignee: Japan as represented by Director General of Agency of Industrial Science & Technology, Japan

[21] Appl. No.: 118,669

[22] Filed: Sep. 10, 1993

[30] Foreign Application Priority Data

Sep. 11, 1992 [JP]  Japan .................................. 4-269349

[51] Int. Cl.6 .......................... C12P 41/00; C12P 7/62
[52] U.S. Cl. ..................................... 435/280; 435/135
[58] Field of Search .......................... 435/280, 134, 135

[56] References Cited

FOREIGN PATENT DOCUMENTS 9220812  11/1992  WIPO .

OTHER PUBLICATIONS

Chulalaksananukul, W. et al., Enzyme Microb. Technol. 15:691–698 (1993).
Grant and Hackh's Chemical Dictionary, p. 580.
Ikushima, Y., et al., Chem. Soc. Japan–Chem. Lett. 1:109–112 (1993).
Steytler, D. C. et al., Enzyme Microb. Technol. 13:221–6 (1991).
Sonomoto, K. et al., Ann. N.Y. Acad. Sci. 542:235–9 (1988).
Langrand, G. et al., Biotechnol. Lett. 12:581–6 (1990).
K. Nakamura, TIBTECH, vol. 8, pp. 288–292 (1990).
M. H. Vermue et al., "Enzyme Microb. Technol.", vol. 14, pp. 649–655 (1992).

*Primary Examiner*—Douglas W. Robinson
*Assistant Examiner*—Sandra Saucier
*Attorney, Agent, or Firm*—Wenderoth, Lind & Ponack

[57] ABSTRACT

A primary terpene alcohol such as citronellol can be enzymatically esterified with a higher fatty acid such as oleic acid in the presence of lipase in an atmosphere of supercritical carbon dioxide as the reaction medium at a high reaction velocity. The influence of the temperature and pressure of the atmosphere on the reaction velocity was studied. When the starting primary terpene alcohol is a racemic compound of the optical isomers having chirality as in ($\pm$)-citronellol, efficient racemic resolution can be achieved by suitably selecting the temperature and pressure in the vicinity of the critical point of carbon dioxide to give the (S)-($-$)-ester having an optical purity of almost 100% when the starting terpene alcohol is ($\pm$)-citronellol.

4 Claims, No Drawings

METHOD FOR ESTERIFICATION OF (S)-CITRONELLOL USING LIPASE IN SUPERCRITICAL CARBON DIOXIDE

BACKGROUND OF THE INVENTION

The present invention relates to a method for the enzymatic esterification reaction. More particularly, the invention relates to an enzymatic esterification reaction of a primary terpene alcohol having a chiral atom and a carboxylic acid as the substrates with an object of racemic resolution, which is industrially important in the organic syntheses, in a high yield and good stereoselectivity.

Certain primary terpene alcohols such as citronellol have chirality and are obtained usually as a racemic compound. In view of the specific biological activity exhibited by each of the optical isomers constituting a racemic compound, it is sometimes desirable to obtain one of the optical isomers by the racemic resolution of the racemic compound. Needless to say, racemic resolution of a racemic compound is generally impossible by an ordinary organic reaction while a possibility of racemic resolution could be expected by a biochemical reaction such as enzymatic reactions.

While stereoselective enzymatic reactions have been reported for the stereoselective synthesis of certain secondary terpene alcohols such as menthol and borneol in an organic solvent such as n-hexane and isooctane in the presence of a lipase, no attempts to cause an enzymatic stereoselective reaction involving a primary terpene alcohol such as citronellol have been successful even by undertaking the same reaction conditions as in the enzymatic reaction for the secondary terpene alcohols.

Turning now to the problem on the reaction medium for biochemical reactions, organic solvents as a reaction medium are highlighted in recent years for various biochemical reactions and number of the cases is increasing year by year for the industrial utilization of biochemical reactions conducted in an organic solvent. One of the objects to use an organic solvent as the reaction medium is to achieve high homogeneity of the reaction mixture as compared with a conventional aqueous reaction medium especially when the solubility of a reactant compound involved is low in an aqueous medium. Use of an organic solvent as a medium for an enzymatic reaction, however, sometimes has a problem that the enzyme is denaturated eventually resulting in deactivation or loss of the enzymatic specificity since the higher-order structure of the enzyme is destroyed as a consequence of the unduly enhanced affinity between the solvent molecules and the hydrophobic groups in the enzyme molecules. Accordingly, it is eagerly desired to develop a reaction medium for an enzymatic biochemical reaction in which oil-soluble or water-insoluble reactant compounds can be readily dissolved while the higher-order structure of the enzyme molecules can be kept intact even by contacting with the medium, for example, in an enzymatic reaction involving a primary terpene alcohol having chirality by which racemic resolution of the racemic compound could be expected as a possibility.

SUMMARY OF THE INVENTION

The present invention accordingly has an object to provide a novel reaction system of an enzymatic reaction involving a primary terpene alcohol having chirality as a substrate by which a possibility can be expected for the racemic resolution of the racemic compound of the substrate compound.

A further object of the invention is to provide an enzymatic method for the esterification reaction of a primary terpene alcohol with a higher fatty acid by which racemic resolution of the substrate compound could be expected to give a possibility of obtaining one of the optical isomers in a high optical purity.

Thus, the method of the present invention for the stereoselective enzymatic esterification reaction of a primary terpene alcohol with a higher fatty acid comprises the step of: contacting the primary terpene alcohol and the higher fatty acid in a reaction medium which is a supercritical atmosphere of carbon dioxide in the presence of a lipase.

In particular, the above defined inventive method is applied to a racemic compound of a primary terpene alcohol having chirality such as citronellol to obtain one of the optical isomers in a high optical purity. When the primary terpene alcohol is (±)-citronellol, for example, (S)-(−)-ester of the citronellol with the higher fatty acid can be obtained in a high optical purity.

DETAILED DESCRIPTION OF THE PREFERRED EMBODIMENTS

As is described above, the most characteristic feature of the inventive enzymatic esterification reaction consists in that the reaction is performed in a specific reaction medium which is a supercritical atmosphere of carbon dioxide in the presence of a lipase.

When a gas is brought into contact with a solid or a liquid, generally speaking, the amount of the solid or liquid transferred to the gaseous phase is very small under the conditions of ordinary temperature and pressure. When the gas constituting the gaseous phase is in a supercritical state, i.e. at a temperature higher than the critical temperature and under a pressure higher than the critical pressure, on the other hand, the amount of the solid or liquid transferred to the gaseous phase is greatly increased. Having a critical temperature of 31.0° C. and a critical pressure of 7.38 MPa (72.80 atmospheres), carbon dioxide in a supercritical state can be a potential reaction medium for a reaction to be conducted under mild conditions involving an organic reactant compound having, for example, a relatively high molecular weight and susceptibility to decomposition at an elevated temperature. Namely, a possibility could be obtained by the use of carbon dioxide in a supercritical state as the reaction medium that the reactants can be rapidly "dissolved" or dispersed in the reaction medium or the by-products can be rapidly eliminated out of the reaction mixture. This possibility means that various useful organic chemical reactions with a high efficiency can be designed in favor of the equilibrium relationship without being restricted by the limitations relative to the solubility behavior of the reactants in the reaction medium at a relatively low temperature.

In this regard, various attempts and proposals have been made in recent years for biochemical reactions conducted in a supercritical atmosphere of carbon dioxide as the reaction medium in place of an organic solvent in view of the above mentioned disadvantages and problems when a biochemical or enzymatic reaction is conducted in an organic solvent as the reaction medium taking into consideration the advantages obtained with supercritical carbon dioxide that good solubility or dispersibility of the oil-soluble or water-insoluble reactant compounds in the reaction medium can be obtained even at a temperature not much higher than the critical temperature 31.0° C. of carbon dioxide without the risk of destroying the higher-order structure of the enzymes.

Directing their attention toward the above mentioned possibility of the advantages obtained by the use of supercritical carbon dioxide as a reaction medium, the inventors have conducted extensive investigations for the enzymatic esterification reaction of a primary terpene alcohol and a higher fatty acid with a foresight that the enzymatic esterification of a primary terpene alcohol having chirality with a higher fatty acid could provide a means for the racemic resolution of the racemic compound.

It has been recently reported that supercritical carbon dioxide exhibits a remarkable dependency of the dissolving power for various kinds of solutes on the temperature and pressure in the vicinity of the critical point. An assumption here is that cohesion of the carbon dioxide molecules takes place to form a cluster at or slightly above the critical point thereof in the vicinal region of the solute molecules. Namely, the interaction between the molecules of the solute and carbon dioxide is greatly increased when the temperature and pressure approach the critical point while the interaction strongly depends on the temperature and pressure. The scope of the present invention consists in the utilization of the strong cohesion of the carbon dioxide molecules in the vicinity of the critical point in the process of an enzymatic reaction. Since the molecules of an enzyme have a larger flexibility than the solute molecules, the higher-order structure of the enzyme would be under a strong pressing influence by the above mentioned cohesion of the carbon dioxide molecules in the vicinity of the critical point possibly to cause alteration in the specificity thereof.

Based on and directing their attention toward the above mentioned presumptive facts, the inventors have conducted an extensive experimentation for the enzymatic esterification of a primary terpene alcohol and a higher fatty acid in a reaction vessel filled with supercritical carbon dioxide using a lipase as the enzyme as immobilized on fine particles arriving, after the studies on the influences of the temperature and pressure on the velocity of the esterification reaction as well as on the optical purity of the esterification product, at a discovery that the velocity of the esterification reaction is greatly increased when the temperature and pressure of the reaction medium approach the critical point and the (S)-(−) ester product having a high optical purity can be obtained as a result of the stereoselective reaction to cause racemic resolution.

One of the substrates in the inventive enzymatic esterification reaction is a primary terpene alcohol and the inventive method is applicable to various kinds of primary terpene alcohols of which the esterification reaction with a higher fatty acid can be conducted with some difficulties. Since the primary object of the inventive method consists in the racemic resolution of a racemic compound, however, a particular primary terpene alcohol to be used in the inventive method is that having chirality such as citronellol, which should be used as a racemic compound, i.e. (±)-citronellol. The other of the substrates in the inventive enzymatic esterification reaction is a higher fatty acid having from 14 to 18 carbon atoms in a molecule exemplified by myristic acid, palmitic acid, stearic acid, oleic acid, linoleic acid and the like. The amount of the higher fatty acid in the reaction mixture relative to the primary terpene alcohol can be about equivalent according to the stoichiometry of the esterification reaction though not particularly limitative.

The enzyme to promote the esterification reaction of the primary terpene alcohol and the higher fatty acid is a lipase. Though not particularly limitative relative to the origin of the lipase, it is preferable to use the lipase obtained from *Candida cylindracea*, i.e. *Candida cylindracea* lipase MY. It is further preferable that the lipase is immobilized on a solid carrier such as fine glass beads and the substrate mixture is passed together with supercritical carbon dioxide through a bed filled with the glass beads carrying the lipase immobilized thereon.

The temperature and pressure of the supercritical carbon dioxide have great influences on the reaction velocity and stereoselectivity of the esterification reaction. The reaction velocity can be increased by increasing the pressure from the critical pressure to about 20 MPa so that, when a high velocity of the esterification reaction is desired, the pressure should be in the range from 15 to 20 MPa and the temperature should be in the range from 35° to 41° C. although a further increase of the temperature to exceed 45° C. is undesirable due to the deactivation of the enzyme. The velocity of the esterification can be higher by more than six times when the reaction is conducted under the above mentioned conditions than the velocity of a similar enzymatic esterification reaction conducted at the same temperature but in water-saturated cyclohexane as the reaction medium. When racemic resolution of the primary terpene alcohol having chirality is the primary object, on the other hand, the temperature and pressure should be as close as possible to the critical point of carbon dioxide so that the inventive enzymatic esterification reaction is conducted preferably at a temperature in the range from 31° to 35° C. or, more preferably, from 31 to 32° C. under a pressure not exceeding 8.5 MPa in consideration of the optimum temperature of lipase which is not higher than 35° C. The efficiency of the racemic resolution of (±)-citronellol is unexpectedly great when the enzymatic esterification reaction is conducted in the vicinity of the critical point of carbon dioxide to give a fatty acid ester of the (S)-(−)-citronellol having an optical purity of almost 100% as the product. Needless to say, the fatty acid ester of the (S)-(−)-citronellol can be converted into (S)-(−)-citronellol by hydrolyzing the fatty acid ester of the (S)-(−)-citronellol.

In the following, the enzymatic esterification reaction of the invention is described in more detail by way of an example.

EXAMPLE.

The enzymatic esterification of (±)-citronellol and oleic acid with lipase was undertaken in an atmosphere of supercritical carbon dioxide as described below. The lipase, i.e. *Candida cylindracea* lipase MY, was immobilized on glass beads having a particle size distribution of 200 to 400 mesh after a pretreatment with glutaraldehyde in the following manner. Thus, 1 g of aminopropyl glass beads were kept in contact at room temperature for 30 minutes with 10 ml of a 25% by weight aqueous solution of glutaraldehyde containing 2.5% by volume of a phosphate buffer solution having a pH of 7.5 followed by filtration and washing with the buffer solution to remove the excess of glutaraldehyde. An aqueous solution of lipase prepared by dissolving 100 mg of a lipase powder in 0.2 ml of deionized water and 5 ml of the buffer solution were poured to the thus pretreated glass beads which were kept standing at room temperature for 4 hours followed by filtration and washing with a phosphate buffer solution having a pH of 7.0. About 55.6% of the enzyme was immobilized on the glass beads in this way.

A reaction column of stainless steel having an inner diameter of 4.6 mm and a height of 130 mm was filled with the thus prepared enzyme-bearing glass beads. The amount of the enzyme supported on the glass beads filling the reaction column was 0.572 g.

Carbon dioxide in a supercritical state was introduced by means of a high-pressure pump at a constant rate of 17 liters/minute calculated for a temperature of 20° C. and a pressure of 101.3 kPa. An equimolar mixture of the substrates, i.e. ($\pm$)-citronellol and oleic acid, was concurrently introduced into the reaction column by means of another high-pressure pump at a rate of 0.03 mmoles/minute relative to the citronellol while the reaction zone in the column was thermostated at a varied temperature in the range from 31.2° to 41.2° C. under a varied pressure in the range from 7.58 to 19.30 MPa controlled by means of a pressure-regulating valve. The reaction mixture coming out of the reaction column was collected during a continued running of the reaction in the above described manner for a period of 120 minutes and gas-chromatographically analyzed for the content of the esterification product, i.e. 3,7-dimethyl-6-octenyl oleate. Further, the reaction mixture was subjected to a column chromatography to isolate the esterification product, of which the optical purity was determined by using a polarimeter assuming a specific rotation $[\alpha]_D$ of $-1.92$ (ethyl alcohol) for an authentic sample of (S)-($-$)-3,7-dimethyl-6-octenyl oleate chemically synthesized from (S)-($-$)-citronellol and oleic acid at 80° C. with sulfuric acid as the catalyst.

Table 1 below shows the reaction velocity in moles/hour.g-enzyme obtained by conducting the enzymatic esterification reaction at a constant temperature of 35.1° C. but under varied pressure of the supercritical carbon dioxide or under a constant carbon dioxide pressure of 8.41 MPa at a varied temperature. As is shown in the table, the isothermal reaction velocity was increased as the pressure is increased from 7.58 MPa to 19.30 MPa rapidly at the initial stage of pressure increase but showing a trend of levelling off while the isobaric reaction velocity was decreased as the temperature is increased from 31.2° to 40.2° C. As a control, the same enzymatic esterification reaction of ($\pm$)-citronellol and oleic acid was undertaken at 35.2° C. in water-saturated cyclohexane as the reaction medium to give a reaction velocity of 2.89 moles/hour.g-enzyme. Table 1 also shows the optical purity of the (S)-($-$)-3,7-dimethyl-6-octenyl oleate. While good racemic resolution could be obtained by the reaction under the conditions in the vicinity of the critical point of carbon dioxide, no racemic resolution took place at all in the above mentioned control experiment of the enzymatic esterification reaction of citronellol carried out in water-saturated cyclohexane.

TABLE 1

| Pressure, MPa | Temperature, °C. | Reaction velocity moles/hour · g-enzyme | Optical purity, % |
|---|---|---|---|
| 7.58 | 35.2 | 3.08 | 23.4 |
| 8.41 | 35.2 | 8.58 | 4.1 |
| 10.15 | 35.2 | 10.18 | 2.1 |
| 15.03 | 35.2 | 13.94 | 2.1 |
| 19.30 | 35.2 | 14.81 | 0.0 |
| 8.41 | 31.2 | 9.27 | 98.9 |
| 8.41 | 40.2 | 6.27 | 2.1 |

What is claimed is:

1. A method for the preparation of (S)($-$)-citronellol by the racemic resolution of ($\pm$)-citronellol which comprises the steps of:
    (a) bringing a mixture of the ($\pm$)-citronellol and a $C_{14}$–$C_{18}$ fatty acid into contact with a lipase in an atmosphere of carbon dioxide in a supercritical state at a temperature not exceeding 35° C. to stereoselectively esterify the (S)($-$)-citronellol giving a fatty acid ester thereof;
    (b) separating the fatty acid ester of (S)($-$)-citronellol from the non-esterified citronellol; and
    (c) hydrolyzing the fatty acid ester of (S)($-$)-citronellol and recovering (S)($-$)-citronellol.

2. The method for the preparation of (S)-($-$)-citronellol as claimed in 1 in which the lipase is *Candida cylindracea* lipase MY.

3. The method for the preparation of (S)-($-$)-citronellol as claimed in 1 in which the fatty acid is oleic acid.

4. The method for the preparation of (S)-($-$)-citronellol as claimed in 1 in which the temperature of the enzymatic esterification reaction in step (a) does not exceed 32° C.

* * * * *